(12) United States Patent
Cabib et al.

(10) Patent No.: US 9,778,174 B2
(45) Date of Patent: Oct. 3, 2017

(54) SINGLE DEVICE FOR GAS AND FLAME DETECTION, IMAGING AND MEASUREMENT

(71) Applicant: CI SYSTEMS (ISRAEL) LTD., Migdal Ha'emek (IL)

(72) Inventors: Dario Cabib, Timrat (IL); Amir Gil, Kiryat Tivon (IL); Moshe Lavi, Nofit (IL)

(73) Assignee: CI SYSTEMS (ISRAEL) LTD., Migdal Ha'emek (IL)

( * ) Notice: Subject to any disclaimer, the term of this patent is extended or adjusted under 35 U.S.C. 154(b) by 71 days.

(21) Appl. No.: 14/983,570

(22) Filed: Dec. 30, 2015

(65) Prior Publication Data

US 2016/0187254 A1    Jun. 30, 2016

Related U.S. Application Data

(60) Provisional application No. 62/098,365, filed on Dec. 31, 2014.

(51) Int. Cl.
*G01N 21/35* (2014.01)
*G01J 3/28* (2006.01)
*G01J 3/02* (2006.01)
*G01N 21/3504* (2014.01)
*G01J 3/36* (2006.01)

(52) U.S. Cl.
CPC ........ *G01N 21/3504* (2013.01); *G01J 3/0205* (2013.01); *G01J 3/2803* (2013.01); *G01J 3/2823* (2013.01); *G01J 3/36* (2013.01)

(58) Field of Classification Search
CPC ...... G01J 3/0205; G01J 3/2803; G01J 3/2823; G01J 3/36; G01N 21/3504
See application file for complete search history.

(56) References Cited

U.S. PATENT DOCUMENTS

2001/0045516 A1* 11/2001 Emanuel ................... B60R 1/00
                                                        250/332
2008/0251724 A1* 10/2008 Baliga ....................... G01J 3/02
                                                        250/338.5

FOREIGN PATENT DOCUMENTS

GB            0973019 A1 *  1/2000  ............. G01J 5/602

* cited by examiner

*Primary Examiner* — Mark R Gaworecki
(74) *Attorney, Agent, or Firm* — Mark M. Friedman

(57) ABSTRACT

A device images radiation from a scene. The scene can include two materials with spectral characteristics in different radiation wavelength regions. A static filtering arrangement includes two filters with different passbands corresponding to the two wavelength regions. An image forming optic forms an image of the scene on a detector. The radiation from the scene is imaged simultaneously through an f-number of less than 1.5 onto two detector pixel subsets. The imaged radiation on one pixel subset includes radiation in one wavelength region. The imaged radiation on the other pixel subset includes radiation in the other wavelength region. Electronic circuitry produces a pixel signal from each detector pixel. The pixel signals include information associated with absorption or emission of radiation in one of the respective wavelength regions by the two materials. The electronic circuitry determines the presence or absence of each of the two materials based on the pixel signals.

20 Claims, 13 Drawing Sheets

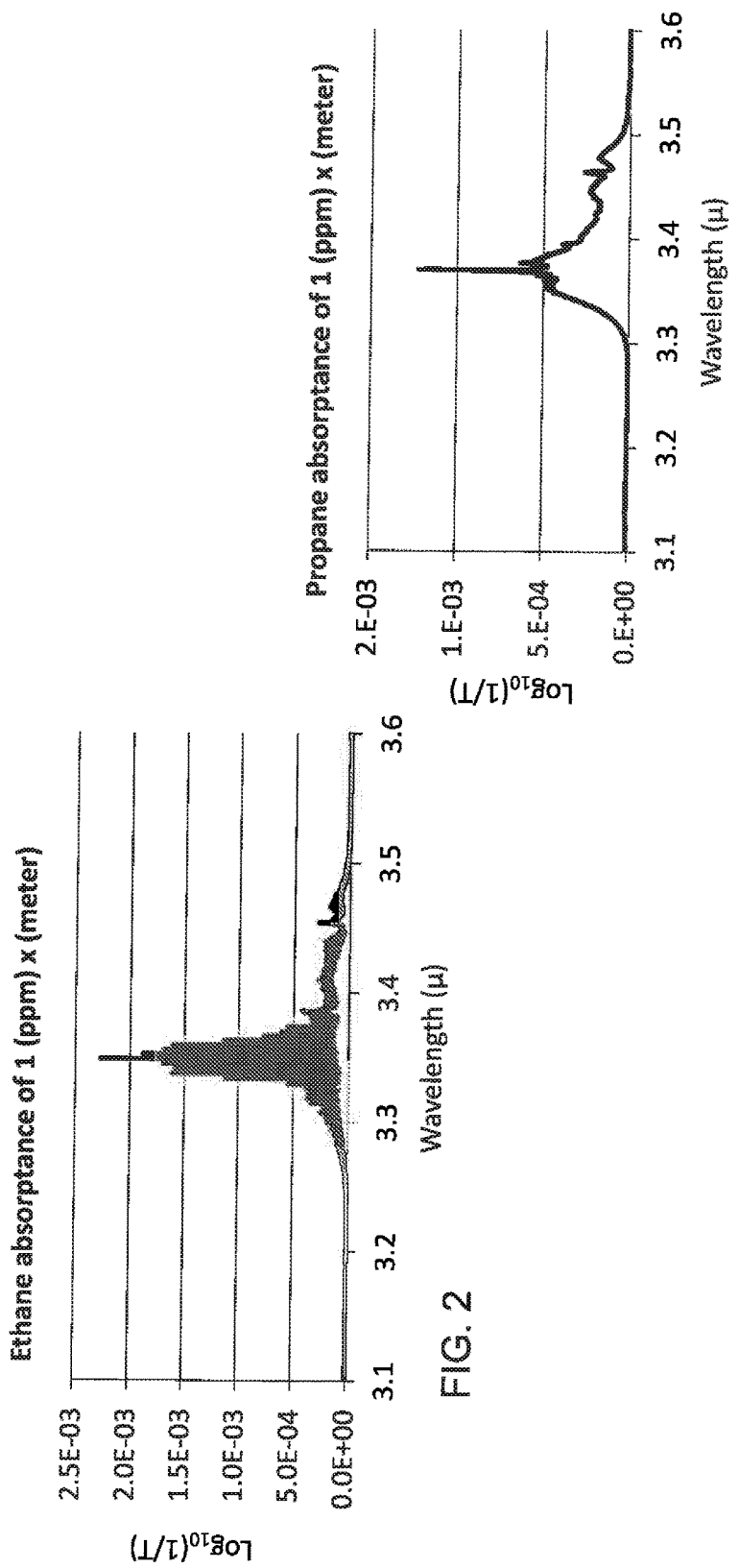

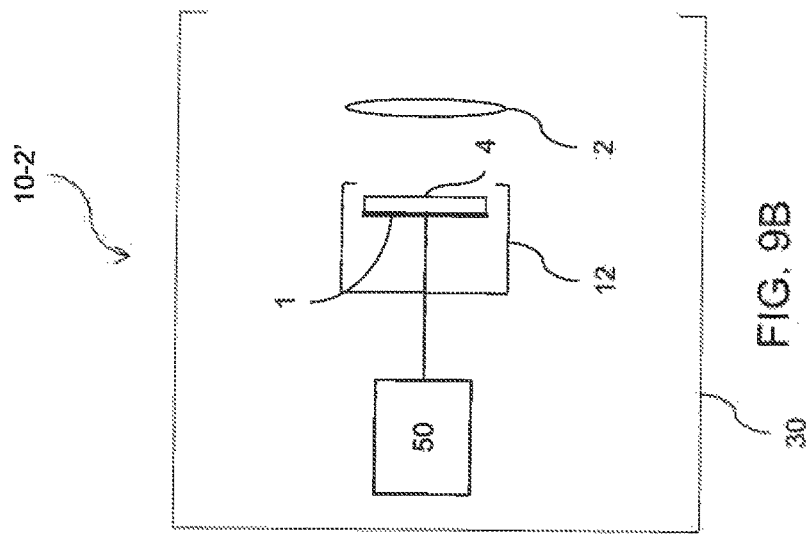
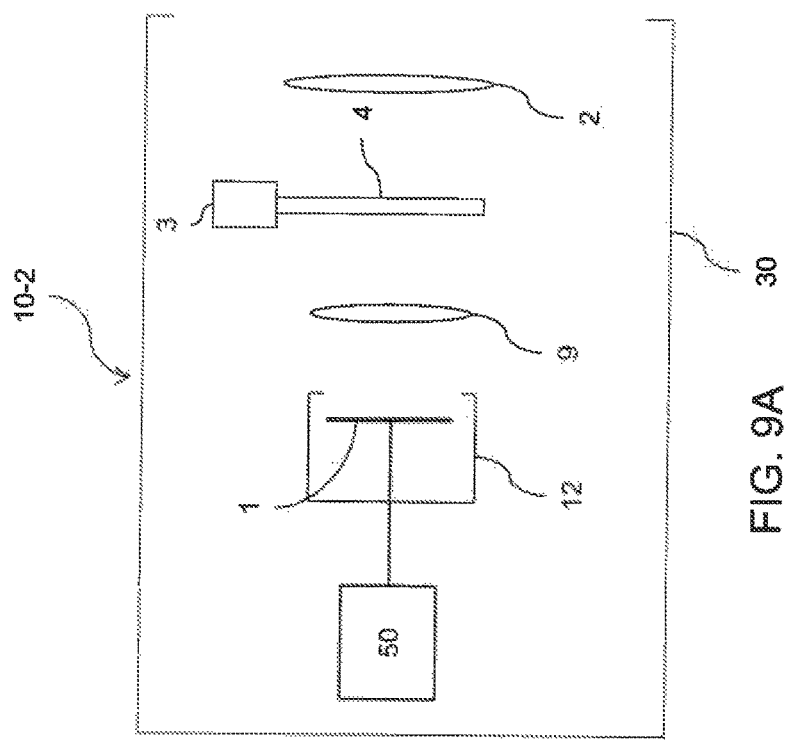

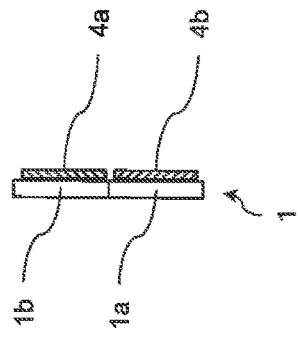
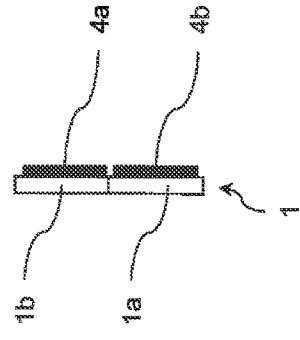
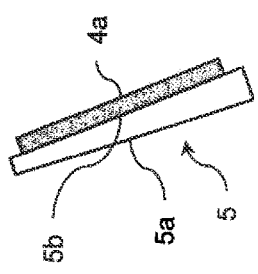
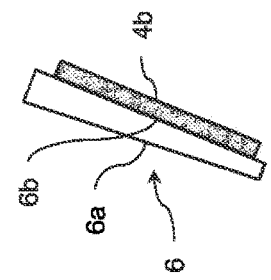
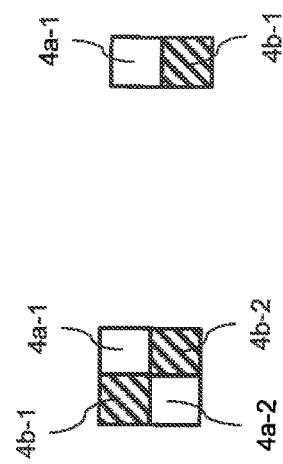
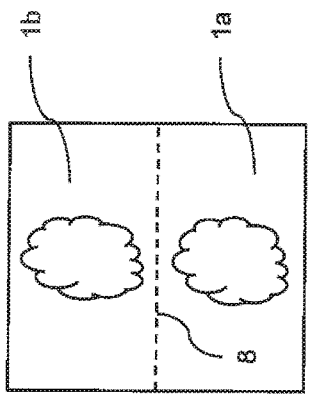

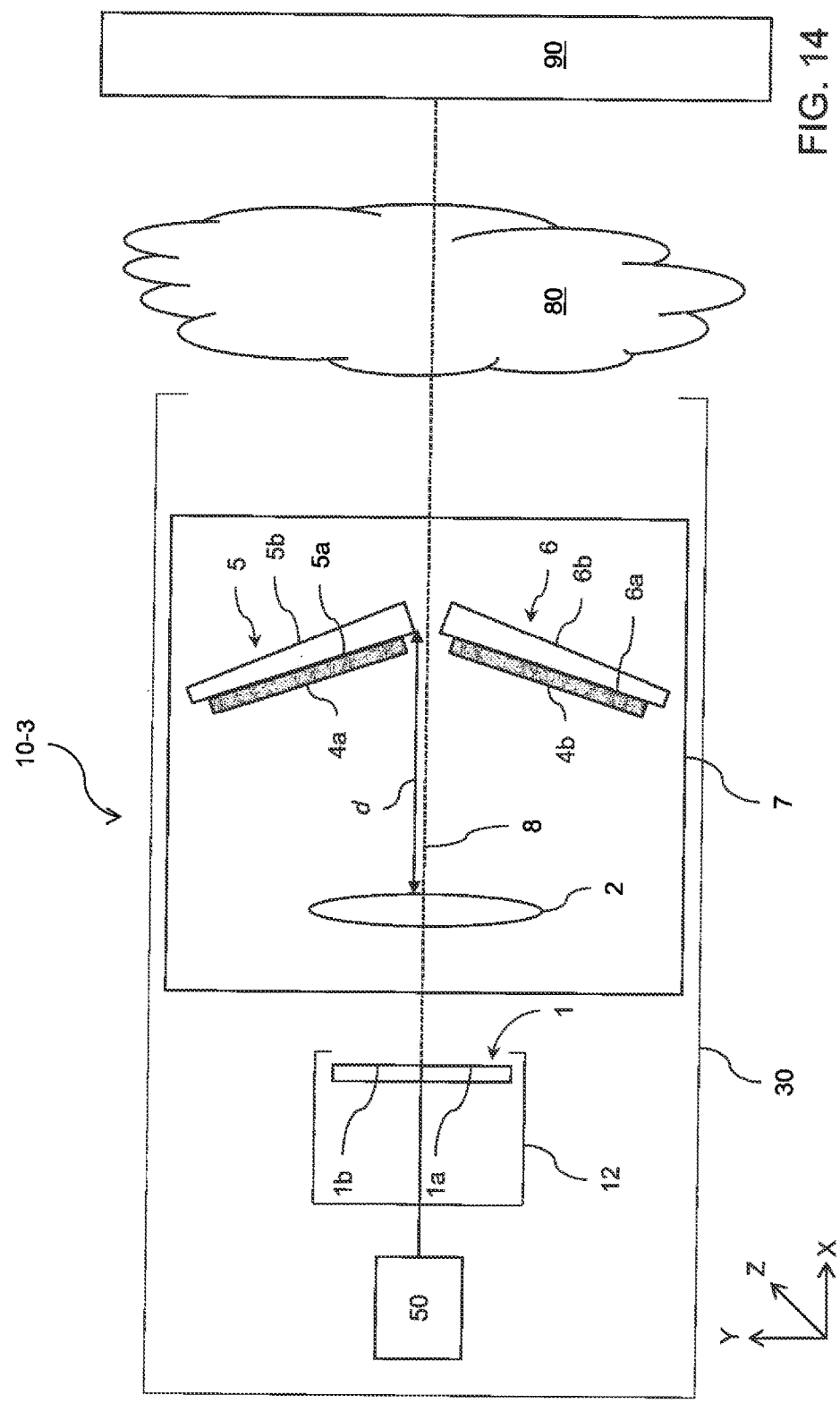

SINGLE DEVICE FOR GAS AND FLAME DETECTION, IMAGING AND MEASUREMENT

CROSS-REFERENCE TO RELATED APPLICATIONS

This application claims priority from U.S. Provisional Patent Application No. 62/098,365, filed Dec. 31, 2014, whose disclosure is incorporated herein by reference. This application is related to the U.S. patent application entitled "Dual Spectral Imager with No Moving Parts" (U.S. patent application Ser. No. 14/949,909), filed on Nov. 24, 2015, the disclosure of which is incorporated by reference in its entirety herein.

TECHNICAL FIELD

The present invention relates to the detection, imaging and measurement of infrared radiation.

BACKGROUND OF THE INVENTION

Industrial plants dealing with mining, production or storage of explosive or flammable gases and vapors such as hydrocarbons (methane, ethane, etc.), fuels of different kinds, hydrogen, acetylene, etc. are in constant danger of accidents. Explosions may cause fires, thus there is inherent danger from both the explosion itself and from the consequent ensuing fires. In addition, fires may result from a plethora of diverse causes, and when occurring in such plants, such fires may themselves cause explosions. The dangers are to both personnel and equipment, and the resulting damages may be in the worst cases loss of human lives and large financial losses to the owners of the plants.

Additionally, the release of the gases in question has a negative impact on the environment. As a result, regulatory laws have been introduced around the world to impose monitoring standards and heavy fines to companies that do not show due diligence in early detection of fires and prevention of inordinate releases of such materials.

The likelihood of explosions increases, up to a point, with increasing gas concentrations. Accordingly, over the past decades a large number of gas concentration measuring devices and fire detection instrumentation has been developed and used in mining, production and storage plants. Until recently only local detectors (for gases) or non-imaging IR and UV detectors (for flames) have been deployed. A gas detector of this type can easily miss the target gas if the gas cloud is present but does not physically meet the position of the detector (or path in case of cloud movement). This is due to the use of contact methods, such as chemical reactions with the gas. In the case of fire detection, the monitor is based on a single detector which does not provide an image of the field (i.e., scene) being monitored. Therefore the monitor cannot provide the necessary information on the location and size of the fire.

Current industry instrumentation does not allow for the detection, identification, and location of the concentration, size and prognosis information of explosive gas or vapor clouds and flames due to incipient fires. Accordingly, current instrumentation cannot meet the additional requirements of being operable from a distance, in harsh environments, usually outdoors, and with minimal false alarms due to signals from other possible infrared sources, such as sun reflections, welding arcs, halogen lamps etc. The alarms provided by such detection instruments may be effectively used by the plant operators to prevent damages and losses of human lives through a number of possible actions. An example of such actions may be partial or total plant shut down, the request of fire department involvement, or other preventive or corrective action.

SUMMARY OF THE INVENTION

The present invention is a passive electro-optical instrument (i.e., device), capable of detecting and imaging a cloud of hydrocarbon gas and/or a flame of burning material from a distance and distinguishing between the two types of materials.

The detection, imaging and measurement of hydrocarbon gas clouds and flames with the same device has a definite cost advantage over other methods using dedicated infrared imagers for each of the two types of events. This solution requires fewer instruments, fewer installations, and less maintenance, and therefore reduced costs. Infrared radiation imaging and measurement technology combined in a single device is a suitable candidate for such an endeavor, since both hydrocarbon gases and flames have spectral absorption and emission signatures in the appropriate range, as will be discussed in subsequent sections of this disclosure.

A key advantage of the device of the present disclosure, among other advantages, is that it provides the capability of event diagnosis without human intervention, so in addition to the above application it can be used as a fixed installation for continuous monitoring and as a hand-held instrument for periodic plant maintenance and repair.

According to an embodiment of the teachings of the present invention there is provided, a device for imaging radiation from a scene the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene; (b) a static filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter; (c) an image forming optical component for forming an image of the scene on the detector, the radiation being imaged simultaneously, through an f-number of less than approximately 1.5, onto a first and second subset of pixels of the detector, the imaged radiation on the first subset of detector pixels including radiation in the first wavelength region and the imaged radiation on the second subset of detector pixels including radiation in the second wavelength region; and (d) electronic circuitry electronically coupled to the detector, the electronic circuitry configured to: (i) produce a pixel signal from each respective detector pixel, each of the pixel signals including information associated with the absorption or emission of radiation in one of the respective wavelength regions by each of the first and second materials, and (ii) determine the presence or absence of the first and second materials based on the produced pixel signals.

Optionally, the first wavelength region includes radiation wavelengths between 3.15 and 3.5 microns, and the second wavelength region includes radiation wavelengths between 4.3 and 4.6 microns.

Optionally, the detector includes a separate first and second detector region, the first detector region including the first subset of detector pixels, and the second detector region including the second subset of detector pixels, and the device further comprises: (e) a radiation directing arrangement for directing radiation from a field of view of the scene through the image forming optical component onto the detector, such that the radiation is separately imaged onto the first and second detector regions through the f-number of less than approximately 1.5.

Optionally, the radiation directing arrangement includes a reflective surface positioned substantially parallel to the optical axis of the device.

Optionally, the first filter is disposed proximate to the first detector region and the second filter is disposed proximate to the second detector region.

Optionally, the first filter is a first plate interposed between the first detector region and the image forming optical component, and the second filter is a second plate interposed between the second detector region and the image forming optical component.

Optionally, the first and second wavelength regions are in the mid wave infrared region of the electromagnetic spectrum and the detector is sensitive to radiation in the first and second wavelength regions.

Optionally, each of the first and second filters is positioned at a distance, along the optical axis of the device, from the image forming optical component, thereby allowing the radiation to be imaged through the f-number of less than approximately 1.5.

Optionally, each of the first and second wedge-shaped components is positioned at a distance, along the optical axis of the device, from the image forming optical component, thereby allowing the radiation to be imaged through the f-number of less than approximately 1.5.

Optionally, the radiation directing arrangement includes first and second substantially wedge-shaped components.

Optionally, the first filter is disposed on one of a first surface or a second surface of the first wedge-shaped component, and the second filter is disposed on one of a first surface or a second surface of the second wedge-shaped component.

Optionally, the first surface of the first wedge-shaped component is a closest surface of the first wedge-shaped component to the image forming optical component, and the first surface of the second wedge-shaped component is a closest surface of the second wedge-shaped component to the image forming optical component, and the second surface of the first wedge-shaped component is a closest surface of the first wedge-shaped component to the scene, and the second surface of the second wedge-shaped component is a closest surface of the second wedge-shaped component to the scene.

Optionally, each of the first and second filters includes a plurality of filter elements, the plurality of filter elements being arranged such that each filter element of the plurality of filter elements of the first filter is adjacent to at least one respective filter element of the plurality of filter elements of the second filter.

Optionally, the determination of the presence or absence of the first and second materials is based on the difference between the pixel signals produced from the first and second subsets of pixels of the detector.

Optionally, the first material is a hydrocarbon gas cloud and the second material is a flame.

Optionally, the electronic circuitry is further configured to: (iii) if the hydrocarbon gas cloud is present, provide a measurement of the path concentration distribution of the hydrocarbon gas cloud based on at least a portion of the pixel signals.

Optionally, the first and second wavelength regions are in the long wave infrared region of the electromagnetic spectrum, and the detector is sensitive to radiation in the first and second wavelength regions.

Optionally, the static filtering arrangement is positioned at an intermediate focal plane, the intermediate focal being between the image forming optical component and a second optical component.

There is also provided according to an embodiment of the teachings of the present invention, a device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene; (b) a filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter; (c) an image forming optical component for forming an image of the scene on the detector through an f-number of less than approximately 1.5; (d) a mechanism for positioning the filtering arrangement relative to the image forming optical component, such that, the radiation is alternately imaged through each of the first and second filters onto the same respective pixels of the detector; and (e) electronic circuitry electronically coupled to the detector, the electronic circuitry configured to: (i) produce, from each detector pixel, a respective pixel signal for each alternation of the radiation imaged through the first and second filters, the pixel signals including information associated with the absorption or emission of radiation in one of the respective wavelength regions by each of the first and second materials, and (ii) determine the presence or absence of the first and second materials based on the produced pixel signals.

Optionally, the first wavelength region includes radiation wavelengths between 3.15 and 3.5 microns, and the second wavelength region includes radiation wavelengths between 4.3 and 4.6 microns.

Optionally, each of the first and second filters includes a plurality of filter elements, the plurality of filter elements being arranged such that each filter element of the plurality of filter elements of the first filter is adjacent to at least one respective filter element of the plurality of filter elements of the second filter.

Optionally, the first material is a hydrocarbon gas cloud and the second material is a flame, and the electronic circuitry is further configured to: (iii) if the hydrocarbon gas cloud is present, provide a measurement of the path concentration distribution of the hydrocarbon gas cloud based on at least a portion of the pixel signals.

Optionally, the first and second wavelength regions are in the mid wave infrared region of the electromagnetic spectrum, and the detector is sensitive to radiation in the first and second wavelength regions.

Optionally, the determination of the presence or absence of the first and second materials is based on, for each respective pixel of the scene, the averaging of a minority subset of pixel signals produced from the radiation imaged through the first filter, and the averaging of a minority subset of pixel signals produced from the radiation imaged through the second filter.

Optionally, the first and second wavelength regions are in the long wave infrared region of the electromagnetic spectrum, and the detector is sensitive to radiation in the first and second wavelength regions.

Optionally, the mechanism is configured to position the filtering arrangement at an intermediate focal plane, the intermediate focal being between the image forming optical component and a second optical component.

BRIEF DESCRIPTION OF THE DRAWINGS

The invention is herein described, by way of example only, with reference to the accompanying drawings, wherein:

FIG. 2 is a plot of the spectral absorptance of ethane gas;
FIG. 3 is a plot of the spectral absorptance of propane gas;
FIG. 9A is a schematic side view illustrating a device for detecting and imaging radiation from a scene in two separate wavelength regions using a checkerboard pattern filtering arrangement, according to an embodiment of the invention.
FIG. 9B is a schematic side view illustrating an alternate configuration of the device of FIG. 9A in which the detecting and imaging of radiation from the scene is accomplished with no moving parts;
FIGS. 12 and 13 show schematic representations of groups of detector pixels corresponding to a single scene pixel, according to an embodiment of the invention;
FIG. 14 is a schematic side view illustrating a device with a wedge configuration for detecting and imaging radiation from a scene in two separate wavelength regions without moving parts, according to an embodiment of the invention;
FIG. 16 is a schematic front view illustrating a detector and the resulting image formed on the detector, according to an embodiment of the invention;
FIGS. 18A and 18B are schematic side views illustrating filtering alternatives of the device of FIG. 14, according to embodiments of the invention;

FIGS. 19A and 19B are schematic side views illustrating filtering alternatives of the devices of FIGS. 14 and 17, according to embodiments of the invention.

DESCRIPTION OF THE PREFERRED EMBODIMENTS

Figure 1:
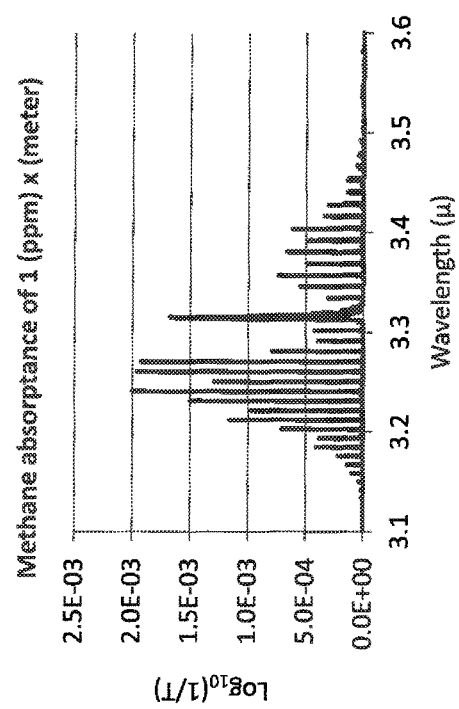
FIG. 1 is a plot of the spectral absorptance of methane gas.

The principles and operation of the device according to the present invention may be better understood with reference to the drawings and the accompanying description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

The present invention is a device for detecting and imaging both a cloud of hydrocarbon gas and/or a flame of burning material. The device performs the detection and imaging from a distance and can distinguish between the two types of events (i.e. hydrocarbon gas and flame of burning material).

As examples, FIGS. 1-3 show the absorptance of 1 (ppm)×(meter) of methane (in units of $Log_{10}$ of inverse transmittance T), ethane and propane in the 2800 to 3200 wavenumbers ($cm^{-1}$) range (equivalent to 3.125 to 3.57 micron range).

Note that ethane and propane above and the other longer chain hydrocarbons butane, pentane and hexane, have absorptance between 3.3 and 3.5 microns while methane absorbs in a wider range, from 3.15 to 3.5 microns. Also note that none of such gases absorb infrared radiation in the 4.3 to 4.6 micron range, where flames emit large amount of radiation.

Figure 4:
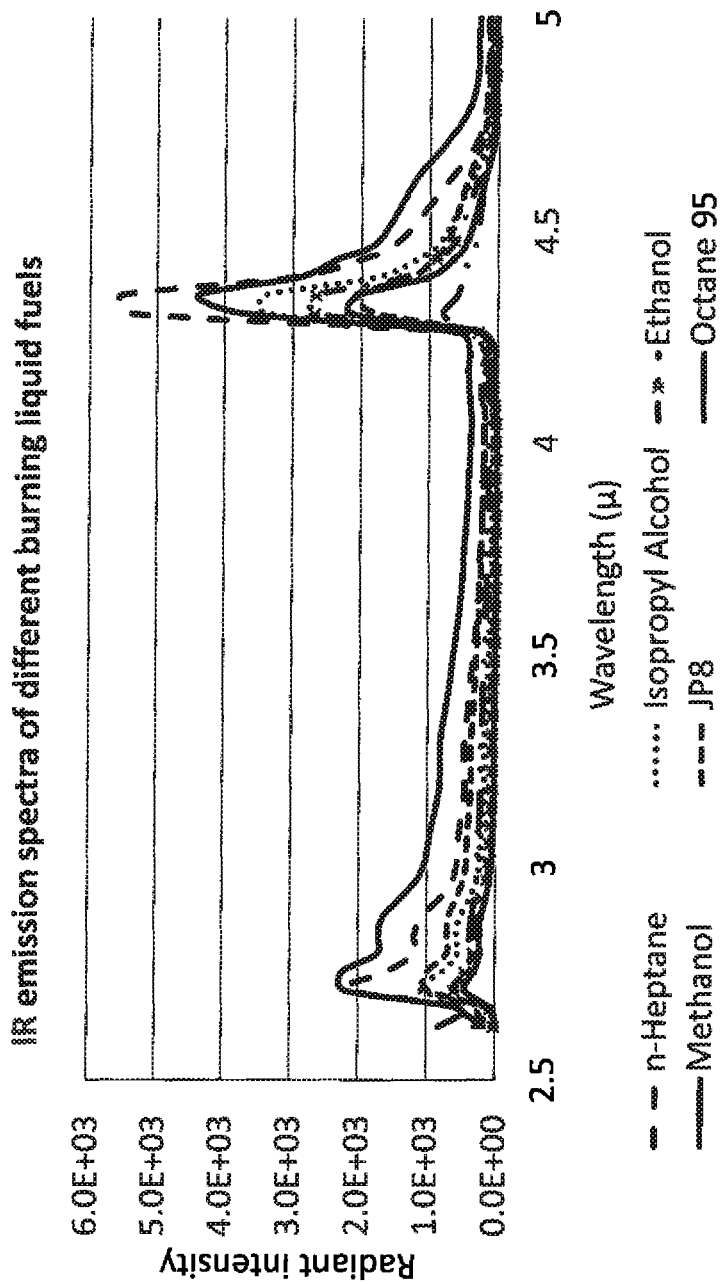
FIG. 4 is a plot of the infrared emission spectra of flames of various burning gas and liquid fuels.

Typical emission spectra of flames due to various liquid fuels such as n-heptane, lead free, jet, diesel and others are shown in FIG. 4. The feature around 2.7 microns is due to self-emission of hot water molecules in the flame, whereas the 4.3-4.7 micron feature is due to the hot $CO_2$ gas in the flame.

Figure 5:
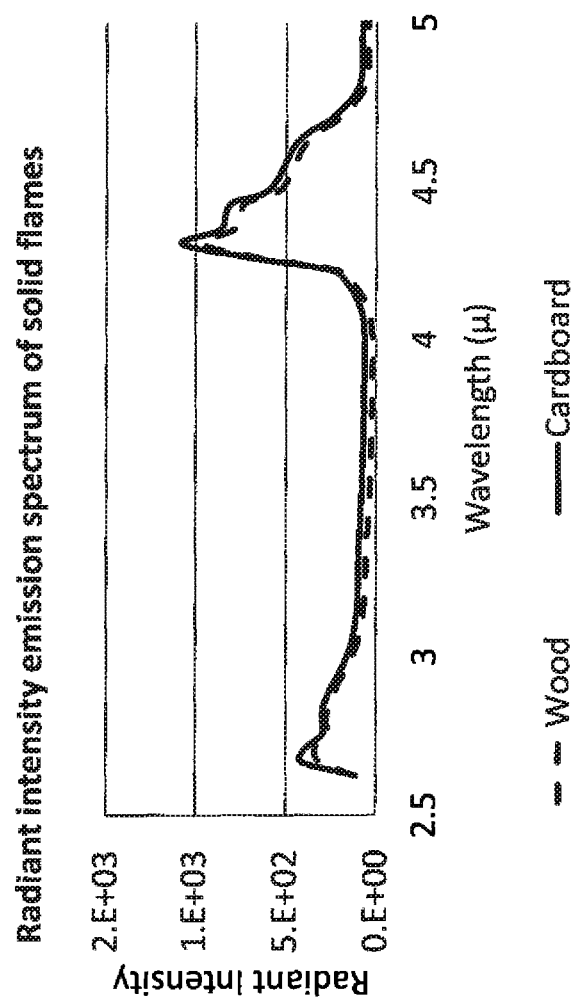
FIG. 5 is a plot of the infrared emission spectra of cardboard and wood.
Figure 7:
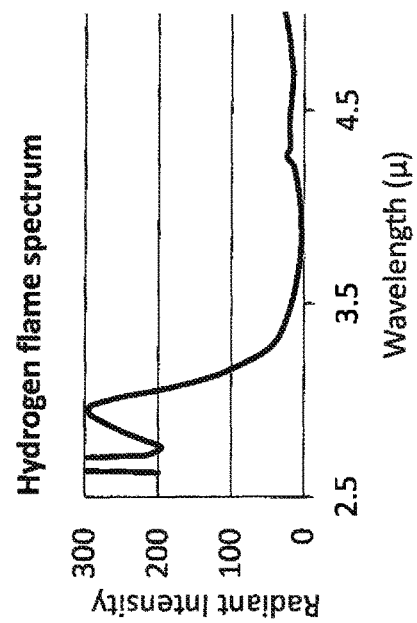
FIG. 7 is a plot of the self-emission spectrum of a hydrogen flame.

Similar infrared spectra of cardboard and wood are shown in FIG. 5. The strong features due to water (near 2.7 microns, due to water and 4.5 microns, due to carbon dioxide) are similar to the flames of liquid fuels of FIG. 4.

Figure 6:
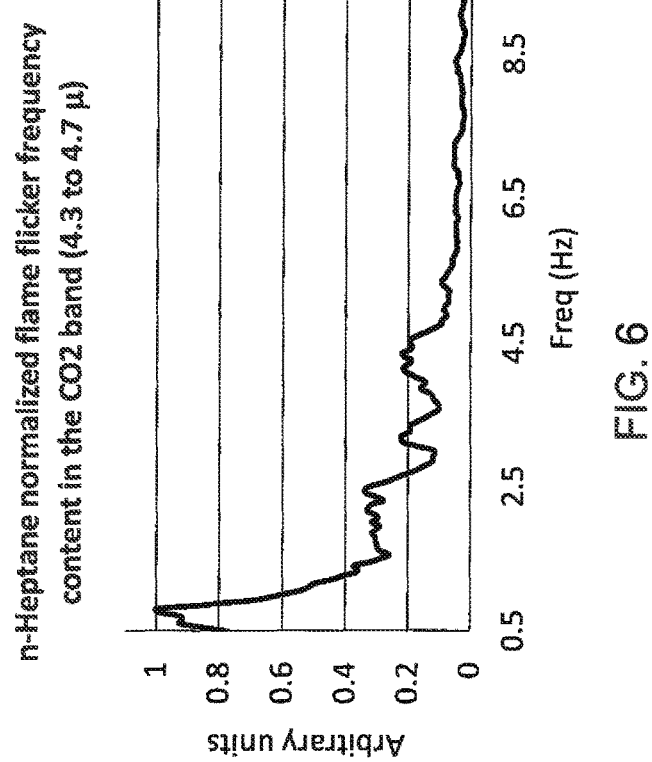
FIG. 6 is a plot of the frequency content of a fuel flame.

Such flames also flicker with characteristic frequencies. Radiometric measurements of n-heptane flame and other fuel flames as a function of time in both the 3 to 5 micron range and 8 to 14 micron range show that 90% of the total emitted energy varies with frequency components up to 5.5 Hz. With a fast enough camera gathering this information, the probability of detection of a liquid fuel flame may be increased. FIG. 6 shows the frequency content of n-Heptane flames as an example.

Note that in the 3 to 5 micron range the hydrogen flame emission is very small compared to the fuel flames emission. It is especially much smaller in the 4.3 to 4.6 micron range, where the flames due to liquid fuels show an especially large emission.

The absorptance data of the hydrocarbon gases are available to the public, for example, from Pacific Northwest National Laboratory in Richland Wash., USA, and are high resolution data. The flame emission spectra and time/frequency behavior have been measured by an SR 5000 N spectroradiometer of CI Systems, an instrument capable of measuring self-emission spectra of objects, calibrated in units of spectral radiance (Watts/((steradian)×(cm$^2$)×(µ)) or spectral radiant intensity in Watts/((steradian)×(µ)).

For the purpose of the present disclosure, it is useful to summarize the spectral data presented in FIGS. 1-7, as will described below.

Hydrocarbon gas absorption spectrum has a significant feature between 3.15 and 3.5 microns in methane and between 3.3 and 3.5 microns in the others. None of these gases have absorption in the 4.3 to 4.6 micron range, where burning flames (except hydrogen) have a strong self-emission feature. The flames, represented by n-heptane in FIG. 6 as an example, show a time behavior of the infrared emission containing frequency components up to 5.5 Hz.

The device of the present disclosure is applicable for use in industrial locations, and is of particular value for both in-door and out-door use, and to provide an alarm in a plant when an explosive gas may be found in above than dangerous amounts, or when a fire has broken out in a space within the field of view of the device. The device is preferably based on an imaging camera (i.e., detector comprised of an array of detector elements) sensitive in the 1 to 4.5 microns spectral range, where both hydrocarbon gases and flames have strong spectral absorption or emission features. The 1 to 4.5 micron spectral range includes portions of the Near Infrared (NIR), Short-Wave Infrared (SWIR), and Mid-Wave Infrared (MWIR) regions of the electromagnetic spectrum. As will be further discussed, the detector array may also be sensitive to radiation in the Long-Wave Infrared (LWIR) region of the electromagnetic spectrum. Elements of the device include the optics to collect this IR radiation from the scene, a number of alternative spectral IR radiation filtering methods, and suitable algorithms especially designed to extract the information needed for detection, real-time imaging and event identification from the resulting pixel signals.

1. General Elements of the Device of the Present Disclosure:

A camera (i.e., detector array) sensitive to infrared radiation in the spectral range preferably between 3 and 4.6 microns is built with collection optics to receive such radiation from a scene and re-image the radiation on the camera through two band pass filters, one covering the range 3.15 and 3.5 microns and one covering the range 4.3 to 4.6 microns. It is well known in the art that a gas cloud interposed between a background and such a camera may be detected and imaged, and its path concentration measured (in units of (ppm$_{volume}$)×(meter)), provided the background temperature is different than the cloud temperature, and the signals produced from the detector array are compared through a so-called in-band filter (transmitting radiation in the absorption wavelength range of the gas, in our case 3.15 to 3.5 microns) and the so-called out-of-band filter (transmitting radiation outside the absorption wavelength range of the gas): in this case the difference between the two signals is positive or negative depending on whether the temperature difference between background and cloud is negative or positive respectively. Analogously, from what is shown in FIG. 4 above, the filter transmitting 4.3 to 4.6 micron radiation is in-band with respect to flames of burning fuels, methane, and solid materials; while the 3.15 to 3.5 filter is out-of-band with respect to the same flames (the signal will be higher in the former and smaller in the latter spectral range). In this way, if the camera pixels are exposed to both filters, either successively or simultaneously by using a split-image method described below, the detection and identification of hydrocarbon gases and flames can be achieved. The appropriate signal differences through the two filters for each pixel will provide an indication as to whether the device is exposed to a flame (large and positive) or to a hydrocarbon gas (much smaller and positive or negative according to the background-object temperature difference).

The following features are important in this invention for becoming used in practice, even though in principle are only optional.

The detector array used in the camera is preferably a PbSe uncooled or thermoelectrically cooled instead of other more expensive cryogenically cooled detectors, such as InSb arrays, which are sensitive in the same spectral range. PbSe detectors are becoming available commercially today. For example, St. Johns Optical Systems in Sanford and Lake Mary, Fla., US, offers such detectors, developed by Northrop Grumman, also in the US. New Infrared Technologies (NIT), a company in Madrid, Spain offers a number of PbSe array detector models.

Time or frequency analysis of the signals, in addition to the in-band-out-of-band comparison may be used in the mathematical algorithms of the device for better distinction between a gas cloud and a flame event, and between a flame and other infrared sources, yielding lower false alarm rate. In fact, flames flicker at characteristic frequencies that may aid in their identification.

Such PbSe detector arrays are sensitive to radiation in the MWIR region of the electromagnetic spectrum. Alternatively, microbolometer type arrays may be used for sensitivity to radiation in the LWIR region of the electromagnetic spectrum.

2a. Gas Measurement:

In the following section, it is shown how the (ppm$_{volume}$)×(meter) of the gas can be measured in a pixel successively exposed to the in-band and out-of-band wavelength range by measuring the radiance difference in these two ranges.

It has been well known for many years that it is possible to detect the presence of a gas in the air by measuring the infrared self-emission of the background of the gas cloud in two different wavelengths, one which is absorbed by the gas and one which is not, provided that the background and gas are not at the same temperature.

The radiance difference R reaching the measuring instrument between the two wavelengths $w_0$ (not absorbed) and $w_G$ (absorbed by the gas), can be expressed in terms of the background radiance B, the gas temperature $T_G$ (usually equal to the air temperature, and we assume that it is known by measurement) and the gas transmittance $t_G$ at the absorbed wavelength as follows:

$$R = B - B^* t_G - (1-t_G)^* Pl(T_G, w_G) = (1-t_G)^* \{B - Pl(T_G, w_G)\} \quad (1)$$

where $Pl(T_G, w_G)$ is the Planck function at temperature $T_G$ and wavelength $w_G$. Two simplifications are used in equation (1) which are not important for the sake of this explanation because the associated phenomena can both be calibrated out in the more general case: i) atmospheric transmittance is assumed to be 1, and ii) background radiance in and out of the gas absorption band are equal.

It is obvious from equation (1) that in the case that B is equal to $Pl(T_G, w_G)$, the radiance difference R is equal to zero, irrespective of the value of $t_G$, and in this case no information can be inferred on the quantity $t_G$. However, if B is different than $Pl(T_G, w_G)$, then equation (1) can be solved for $t_G$ as follows:

$$t_G = 1 - \frac{R}{B \cdot Pl(T_G, w_G)} \quad (2)$$

All parameters on the right hand side of equation (2) are known: B is known because it is measured in the non-absorbing wavelength $w_0$, Pl is known because $T_G$ is measured and $w_G$ is known, and R is measured. Therefore $t_G$ is known from equation (2). If the molecular absorptance, $A_G$, of the specific gas being monitored is known from the literature at $w_G$, then $t_G$ gives a measure of the product of average gas volume concentration in the cloud, multiplied by the thickness of the cloud itself, or the so called concentration times length (or path concentration) value of the cloud. In fact, by the Lambert-Beer law as follows:

$$t_G = e^{-nA_G l} \quad (3)$$

where l is the path length or thickness of the cloud and n is the average volume concentration of the gas being measured in the cloud, both corresponding to a specific pixel being examined. Equation (3) can then be inverted to yield the value of the product nl for the particular pixel in question:

$$nl = \frac{1}{A_G} \ln\left(\frac{1}{t_G}\right) \quad (4)$$

If $t_G$ in (2) is measured to be less than 1, then nl in (4) is finite and there is gas in the region of the pixel in question, in the amount nl ($ppm_{volume}$)×(meter). If $t_G$ from (2) is equal to 1, then nl=0 in (4), and there is no gas. Note that $t_G$ values less than 0 or larger than 1 are not physical, since $t_G$ is a transmittance and is therefore bounded between 0 and 1.

2b. Flame Measurement:

In the case that a flame is present in a pixel of the scene instead of a gas cloud, the detector pixel signal $S_{flame}$ is nearly zero when exposed to filter $w_G$ and high when exposed to filter $w_0$. This is due to the definition of the band pass of the two filters 4a and 4b and to the shape of the flame emission spectra as shown in FIG. 4. The difference of the signals measured through the two filters 4a and 4b, or simply the $w_0$ signal (from the filter 4b), indicates the presence or absence of the flame in the corresponding scene pixel.

In the following sections, the various embodiments of a device will be presented with different optical and filtering configurations for achieving the gas concentration measurement and flame detection functionality previously discussed.

Figure 8:
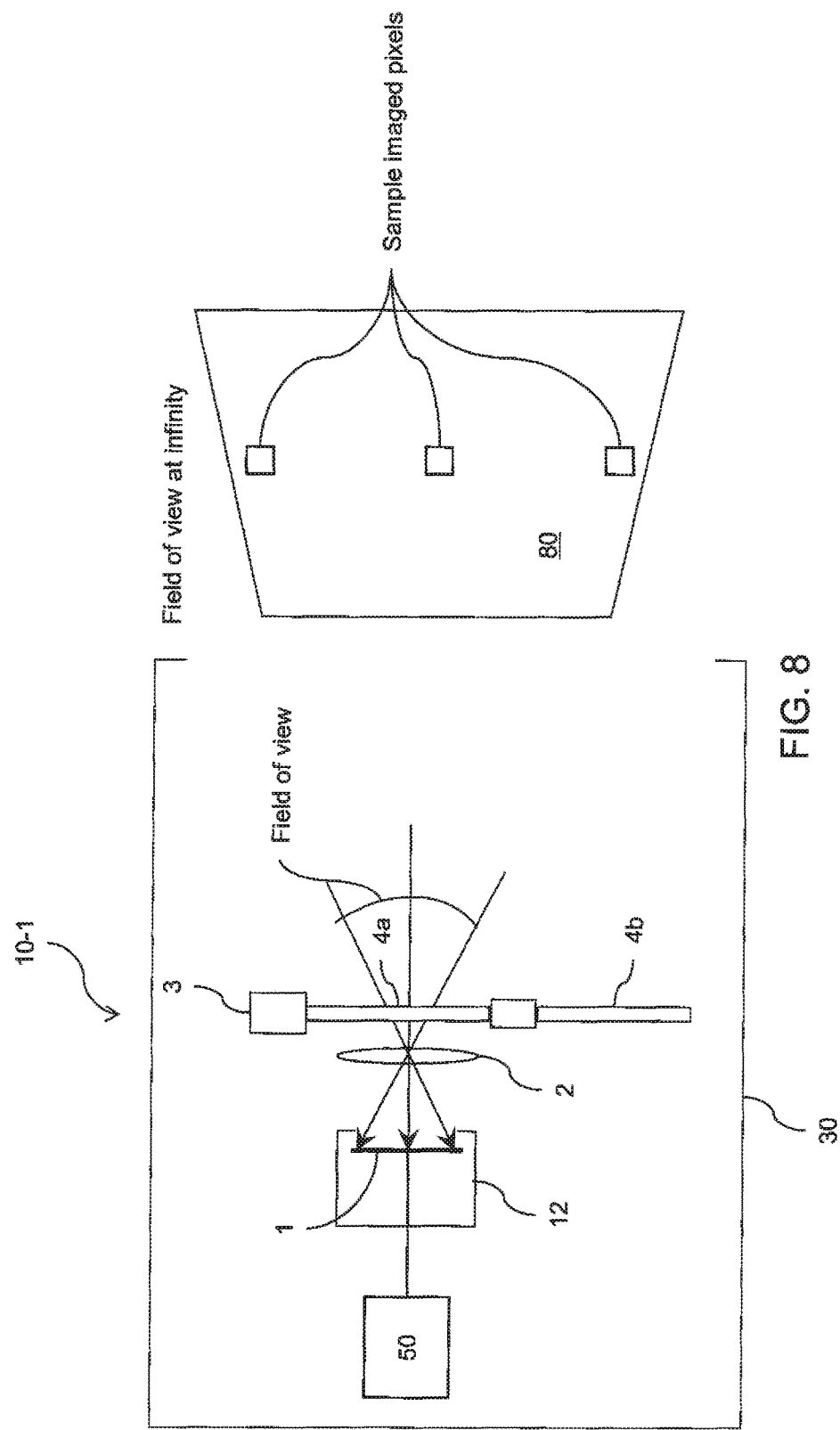
FIG. 8 is a schematic side view illustrating a device for detecting and imaging radiation from a scene in two separate wavelength regions, according to an embodiment of the invention.

3a. Successive Exposure to in-Band and Out-of-Band Filtering:

FIG. 8 depicts an embodiment of a device 10-1 for detecting and imaging a cloud of hydrocarbon gas and a flame (i.e, a scene 80). The device 10-1 includes an objective lens 2 (i.e., collection optics), positioned in front of a detector array 1 and a two-position filter holder or wheel 3 containing two filters (a first filter 4a and a second filter 4b), either in front of the objective lens 2 or between the objective lens 2 and the detector array 1. The first filter 4a, centered at $w_G$, is the in-band gas filter with a pass band between 3.15 and 3.5 microns or between 3.3 and 3.5 microns, or an optimized range between 3.15 and 3.5 microns. The second filter 4b, centered at $w_0$, is the out-of-band gas filter with a pass band between 4.3 and 4.6 microns. The first filter 4a (i.e., the filter centered at $w_G$) serves also as the out-of-band flame filter; while the second filter 4b (i.e., the filter centered at $w_0$) serves also as the in-band flame filter. The filter holder or wheel alternates the two filters in the optical train, successively exposing the detector to the two different spectral ranges. Only the principal rays of the central, top and bottom pixels of the field of view (FOV) are shown. The filters 4a and 4b can be alternately placed between the lens 2 and the detector array 1 or between lenses in a multiple lens system design.

Note that the configuration of the device 10-1 as shown in FIG. 8 can be preferably designed with a large numerical aperture of the objective lens 2 to exploit the best possible detector sensitivity (or low f-number, which is in general kept as close to 1 as possible, especially when using uncooled infrared detector arrays). Accordingly, it is preferred that the objective lens 2 of the device 10-1 has an f-number less than 1.5, and as close to 1 as possible (i.e., fl 1.5 or less). A different configuration, using a dichroic beamsplitter to split the incoming beam into two beams to be filtered separately in the two wavelengths and two separate detectors can be used, but would be more expensive because of the additional detector cost. A further similar configuration using, besides the dichroic filter, an additional beam combiner and chopper may be used to limit the design to the single array detector, but in this case the chopper, needed to switch between the two wavelengths in synchronization with the detector frame capture rate, is a low reliability moving part. These last two configurations require more complicated optics to avoid decreasing the numerical aperture of the focusing optics at the detector and degrade the device sensitivity.

Note that a whole frame image of the scene 80 is exposed to only one of the two band pass filters 4a and 4b in succession. The information needed for gas or flame detection and imaging is achieved by the acquisition of at least two frames while the two filters 4a and 4b are successively positioned in the optical train by the rotation or translation of the holder or wheel 3, in such synchronization that each frame is acquired through one of the filters (4a or 4b). The sequence of exposure to the two filters 4a and 4b can be repeated as many times as desired, whether for averaging to achieve higher signal to noise ratio or for any other reason. The sequence may be composed also by several frames through one of the filters and then several frames through the other filter, instead of alternating frames.

Image acquisition electronics 50 are electrically coupled to the detector array 1 for processing output from the detector array 1 in order to generate and record signals corresponding to the detector elements (i.e., pixels) for imaging the scene 80. The image acquisition electronics 50 includes electronic circuitry that produces corresponding pixel signals for each pixel associated with a detector element. As a result of the radiation being imaged on a multiple of detector elements, the image acquisition electronics 50 produces multiple corresponding pixel signals.

Figure 20:
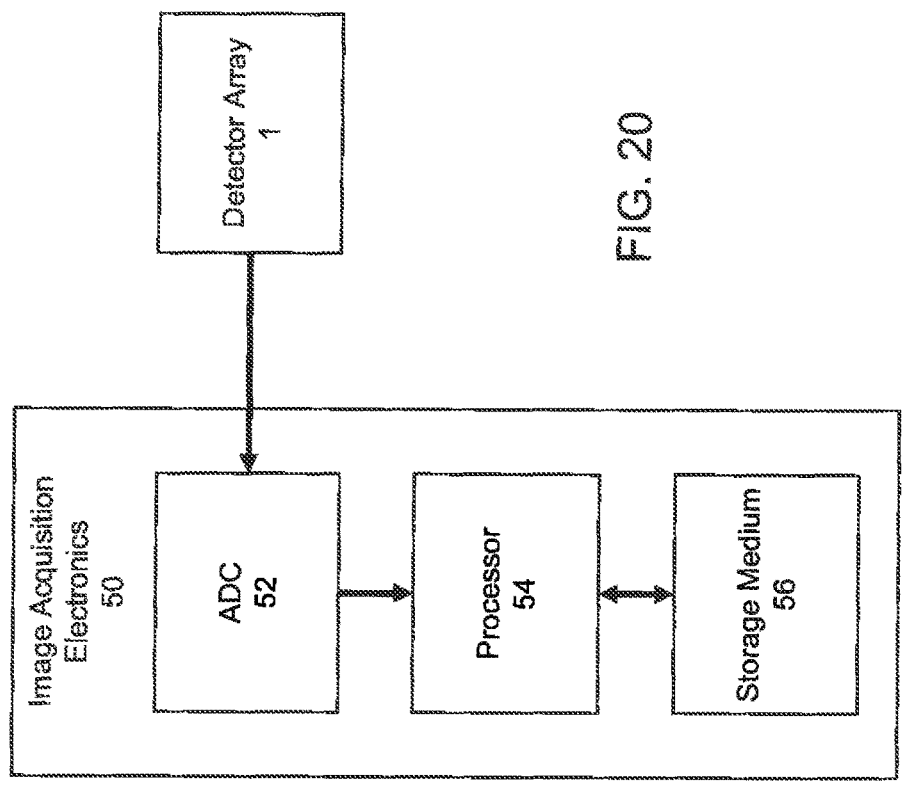
FIG. 20 is a block diagram of image acquisition electronics coupled to a detector array, according to an embodiment of the invention.

As shown in FIG. 20, the image acquisition electronics 50 preferably includes an analog to digital conversion module (ADC) 52 electrically coupled to a processor 54. The processor 54 is coupled to a storage medium 56, such as a memory or the like. The ADC 52 converts analog voltage signals from the detector elements into digital signals. The processor 54 is configured to perform computations and algorithms for determining and/or indicating the presence or absence of the gas cloud path concentration distribution and/or flame, as well as imaging and measuring the gas cloud path concentration distribution and/or flame, as described in Sections 2a and 2b, based on the digital signals received from the ADC 52.

The processor 54 can be any number of computer processors including, but not limited to, a microprocessor, an ASIC, a DSP, a state machine, and a microcontroller. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions.

The above mentioned components of the device 10-1 are positioned within a casing defined by internal walls 30 of the device 10-1. Furthermore, the detector array 1 is preferably maintained within a detector case 12, which in turn is positioned within the casing of the device 10-1.

3b. Exposure to in-Band and Out-of-Band Filtering by Pattern Filtering:

FIGS. 9A and 9B depict different configurations of a device 10-2 and 10-2' which are alternative embodiments of the device 10-1, which uses an alternate method of switching the exposure of the pixels of the detector to the two band pass filters centered at wavelengths $w_G$ and $w_O$ by "patterned filtering". This method may be implemented both statically (with some degree of loss of spatial resolution as explained below) or dynamically by movement of an optical filtering device. In the latter case the extent of movement is much smaller in amplitude than in the method of Section 3a, and can be performed with a simpler and cheaper motor, like a piezoelectric oscillator, instead of a rotary or translatory motor like in the previous section.

Figure 10:
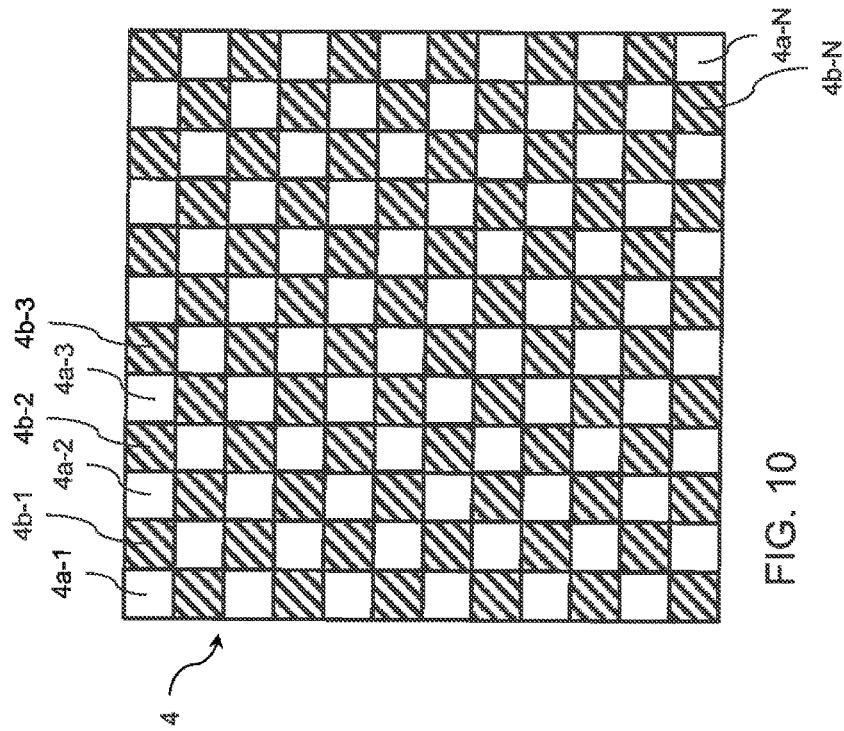
FIG. 10 is a schematic representation of a checkerboard pattern filtering arrangement for performing detection and imaging of the radiation from the scene using the configurations of the device of FIGS. 9A and 9B.

Referring to FIG. 10, a checkerboard patterned filter 4 is implemented as the optical filtering device. The filter 4 can be used as a replacement for the two filters 4a and 4b of FIG. 8, and may be placed in an intermediate focal plane (FIG. 9A), an image plane of the scene, which is then re-imaged on the detector array, or on or as close as possible to the detector plane itself (FIG. 9B). For the device 10-2, the positioning of the checkerboard patterned filter 4 in an intermediate focal plane is depicted schematically in FIG. 9A. The lens system of the device 10-2 includes the objective lens 2 and a re-imaging optical lens 9 (i.e., re-imaging optics). For the device 10-2', the positioning of the checkerboard patterned filter 4 on the detector plane is depicted schematically in FIG. 9B. The size of the squares on the board is optically matched to the size of the detector pixel, and each square is coated so that a particular square corresponds to one or the other of the filters 4a and 4b.

In FIG. 10, the white squares (4a-1, 4a-2, . . . , 4a-N) correspond to the first filter 4a (i.e., the filter centered at $w_G$). Each white square (4a-1, 4a-2, . . . , 4a-N) represents an individual element of the first filter 4a (i.e., the filter centered at $w_G$). Similarly, the diagonally hatched squares (4b-1, 4b-2, . . . , 4b-N) correspond to the second filter 4b (i.e., the filter centered at $w_O$). Each diagonally hatched square represents an individual element of the second filter 4b (i.e., the filter centered at $w_O$). The elements of the first and second filters 4a and 4b occupy the entire detector plane. The filter 4 is oscillated the length (i.e., amplitude) of a square along the horizontal or vertical direction relative to the detector plane. This successively exposes each detector pixel to one or the other of the band pass filters. The oscillation is performed in synchronization with the detector frame acquisition (i.e., the image acquisition electronics 50) in order to provide the necessary scene information for performing the gas measurement and flame detection described in Sections 2a and 2b above, as carried out by the processor 56 of the image acquisition electronics 50.

Figure 11:
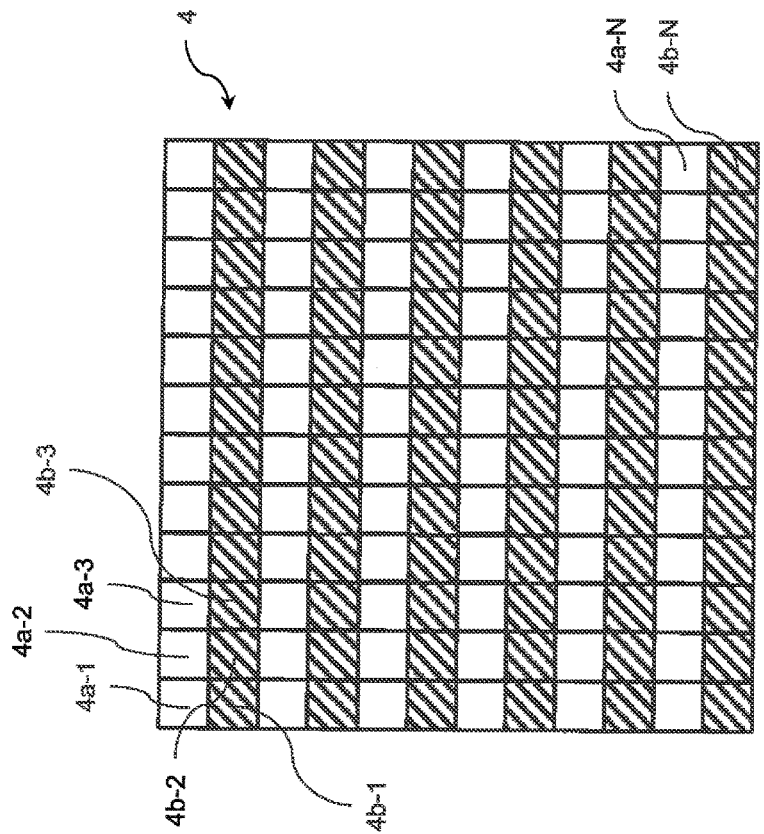
FIG. 11 is a schematic representation of an alternate configuration of the checkerboard pattern filtering arrangement of FIG. 10, according to an embodiment of the invention.

The filter combination shown in FIG. 10 can be alternatively implemented with alternating rows or columns of the elements centered at $w_G$ and $w_O$ instead of a checkerboard, as in FIG. 11. In the implementation of the filter 4 depicted in FIG. 11, the movement of the filter 4 is in the vertical direction relative to the detector plane. The movement amplitude is equal to the length of one square, as previously described.

Note that many other similar configurations may be conceived, as for example the alternating stripes of FIG. 11 arranged in columns instead of rows. In this case the movement is in the horizontal direction relative to the detector plane.

A checkerboard or stripe configuration as in FIGS. 10 and 11 may be also static, either on an intermediate focal plane as mentioned above, or positioned very close to the detector plane, so that each square or row is exactly spatially registered with each pixel or row of pixels, respectively. As mentioned, such a configuration of the device 10-2' is depicted schematically in FIG. 9B. In this case the spatial resolution or field of view is decreased because one scene pixel is now made of at least two or four (or more) detector pixels. In order to obtain the information on the gas or flame presence, the signals of detector pixels corresponding to either of the band pass filters is summed together and averaged. The summing and averaging of the signals may be executed by the processor 54. Accordingly, the entire scene 80 is imaged onto the detector 1. The neighboring detector pixels produce signals, via the image acquisition electronics 50, which correspond to the same portion of the scene 80 as filtered through each of the filters 4a and 4b.

In FIG. 12, a group of four detector pixels is shown which correspond to a single scene pixel. The signals of the pixels filtered through the white squares (i.e., 4a-1 and 4a-2 corresponding to the filter centered at $w_G$) are averaged to obtain the in-band signal of the scene pixel. Similarly, the signals of the pixels filtered through the diagonally hatched squares (i.e., 4b-1 and 4b-2 corresponding to the filter centered at $w_O$) are averaged to obtain the out-of-band signal of the scene pixel. In such a configuration, the number of scene pixels is reduced by a factor of two in both the vertical and horizontal directions relative to the detector plane.

In FIG. 13, a group of two detector pixels is shown which correspond to a single scene pixel. In such a configuration, no averaging is necessary, and the number of scene pixels is reduced by a factor of two only in the vertical direction relative to the detector plane.

As should be understood, both checkerboard patterned filter implementations as depicted in FIGS. 10 and 11 can be used with of the devices 10-2 and 10-2', depicted in FIGS. 9A and 9B, respectively. Furthermore, the objective lens 2 of the devices 10-2 and 10-2' can be designed with a large numerical aperture (i.e., fl 1.5 or less and as close as possible to fl 1) similar to the objective lens of the device 10-1.

Similar to the device 10-1, the components of the devices 10-2 and 10-2' are positioned within a casing defined by internal walls 30 of the respective devices 10-2 and 10-2'. Also similar to the device 10-1, the detector array 1 of each of the respective devices 10-2 and 10-2' are preferably maintained within a detector case 12.

3c. Exposure to in-Band and Out-of-Band Filtering by Split Image Wedge Configuration:

FIG. 14 shows an embodiment of a device 10-3 that uses an optical configuration referred to as a "split image wedge" configuration. The object (scene 80 against the background 90) on the right side is imaged on the detector plane through the two wedge-shaped components (5 and 6) and the objective lens 2, so that two images of the scene 80 and the background 90 are formed on two halves of the surface of the detector array 1 (a first half 1a and a second half 1b), as shown in FIG. 16. The scene 80 and the background 90 are imaged simultaneously on two halves of the detector plane, forming two identical images. The two images are formed through the two band pass filters centered at $w_G$ and $w_0$, respectively, implemented as coatings 4a and 4b, respectively, so that each scene pixel is measured through an in-band and an out-of-band filter by two different detector pixels at the same time.

The wedge shaped components 5 and 6 together with the objective lens 2 constitute collection optics 7. Most preferably, the detector array 1 of the device 10-3 is a PbSe type array sensitive to radiation in the MWIR region of the electromagnetic spectrum.

The device 10-3 has the advantage that no filter movement is required and that the in-band and out-of-band signals are acquired at the same time. This may improve on potential drifts between the two signals due to gas cloud movement. The disadvantage is that the detector area is exploited for one half of the field of view that could be obtained with the same objective optics and without the wedges. Similar to the device 10-1 of FIG. 8 and the devices 10-2 and 10-2' of FIGS. 9A and 9B, respectively, the device 10-3 includes image acquisition electronics 50 for generating digital signals and for performing computations and algorithms for determining and/or indicating the presence or absence of the gas cloud path concentration distribution and/or flame, as well as imaging and measuring the gas cloud path concentration distribution and/or flame.

The same infrared radiation from the scene 80 is imaged onto each of the two detector regions 1a and 1b, with each region of the detector imaging the scene 80 in a different wavelength range.

Figure 15:
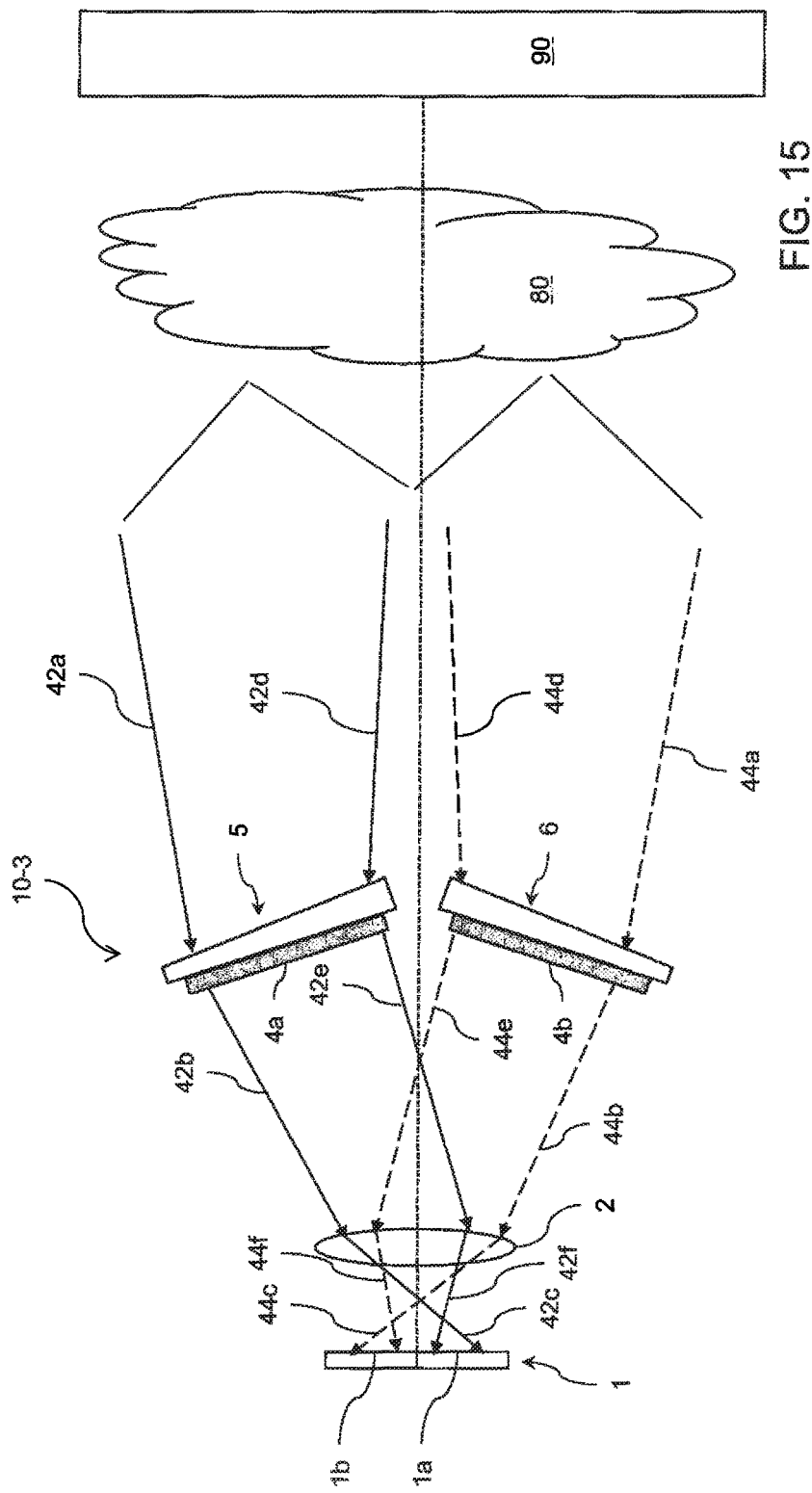
FIG. 15 is a schematic side view illustrating the traversal of incident rays from the scene and the scene background through the device of FIG. 13.

FIG. 15 depicts the traversal of incident rays 42a-42f and 44a-44f from the scene 80 to the detector array 1. The broken lines between the scene 80 and the device signifies that the distance between the scene 80 and the device as depicted in FIG. 15 is not to scale. In general, the distance between the scene 80 and the device is much larger than the size of the device itself, and is typically on the order of tens or hundreds of meters. Additionally, the broken line signifies that the two bundles of rays 42a, 42d and 44a, 44d both originate from the entire scene and not from one half of the scene.

Note that although only four incident rays 42a, 42d and 44a, 44d are depicted in FIG. 15 (these are the marginal rays which define the field of view of the device 10-3 in the plane of the cross section defined by the plane of the paper), it should be apparent that additional similar incident rays originating from the scene 80 are present and follow a path of traversal similar to the rays as described above. An exception is that ray components parallel to the plane of the page undergo deflection by the wedge, while the ones perpendicular to it do not undergo deflection. As such, reference to the incident rays 42a, 42d and 44a, 44d implicitly applies to all such similar incident rays originating from the scene 80 within the field of view.

The objective lens 2 focuses radiation deflected at an angle by the wedge-shaped components 5 and 6 on the detector array 1 to form two simultaneous and separate images of the scene 80 with the background 90, each image being formed on one half of the detector surface. As such, the radiation from the scene 80 and its background 90 is imaged separately and simultaneously onto the detector regions 1a and 1b.

The scene 80 and the background 90 is imaged by the device 10-3 with no moving parts while maintaining a high numerical aperture and low f-number (fl 1.5 or less) at the detector array 1. This is accomplished by positioning each of the first and second wedge-shaped components 5 and 6 at a minimum fixed distance d from the objective lens 2 along the optical axis of the device 10-3. Positioning the wedge-shaped components 5 and 6 at a sufficiently large enough distance from the objective lens 2, in combination with the above mentioned deflection angles, allows for the low f-number (high numerical aperture) at the detector array 1 to be maintained. This corresponds to high optical throughput of the device 10-3. As a result, the same radiation from the scene is deflected by the wedge-shaped components 5 and 6 toward the objective lens 2 and imaged on the detector regions 1a and 1b through an f-number of the collection optics 7 which can be maintained close to 1 (fl 1) without having to decrease the focal length for increase the aperture diameter D. Accordingly, the minimum distance d which provides such high optical throughput can be approximately lower bounded by:

$$d > \frac{D}{2\tan\left(\frac{\theta}{2}\right)} \quad (5)$$

where D is the aperture diameter of the objective lens and $\theta$ is the vertical field of view of the objective lens.

Having a large numerical aperture (low f-number) provides higher sensitivity of the detector array 1 to the radiation from the scene 80, and less sensitivity to radiation originating from within the internal walls of the device 10-3, the collection optics 7, and the optical components themselves.

As a result of positioning the wedge-shaped components 5 and 6 at the distance d, the vertical fields of view of the wedge-shaped components 5 and 6 are approximately half of the above mentioned vertical field of view of the objective lens 2.

The wedge-shaped components 5 and 6 are preferably positioned symmetrically about the optical axis, such that each is positioned at the same distance d from the objective lens 2, and each is positioned at the same angle relative to the optical axis. Such a design ensures that the same amount of radiation is imaged on the detector regions 1a and 1b via the objective lens 2 from the wedge-shaped components 5 and 6.

As previously mentioned, the radiation from the scene 80 which is imaged onto the first detector region 1a only includes one of the wavelength ranges. The radiation from the scene 80 which is imaged onto the second detector region 1b only includes the other one of the wavelength ranges. This is accomplished by positioning the filters 4a and 4b in the optical train.

In the exemplary implementation shown in FIGS. 14-16, the radiation from the scene 80 imaged on the first detector region 1a only includes the in-band radiation from the gas filter 4a (i.e., the filter centered at $w_G$), and the radiation from the scene 80 imaged on the second detector region 1b only includes the in-band radiation from the flame filter 4b (i.e., the filter centered at $w_0$). Accordingly, the first filter 4a filters radiation in spectral ranges outside of the first wavelength range (i.e., stop band of the filter centered at $w_G$) and the second filter 4b filters radiation in spectral ranges outside of the second wavelength range (i.e., stop band of the filter centered at $w_0$). Thus, the radiation from the scene 80 that is directed by the first wedge-shaped component 5 to be imaged on the first detector region 1a includes only the in-band radiation from the gas filter 4a, and the radiation from the scene 80 that is directed by the second wedge-shaped component 6 to be imaged on the second detector region 1b includes only the in-band radiation from the gas filter 4a.

As previously mentioned, the surface of the detector array 1 is divided into the two aforementioned regions by a dividing plane 8 as shown in FIG. 16. FIG. 14 includes a non-limiting exemplary representation of the Cartesian coordinate system XYZ in which the detector plane is parallel to the YZ plane. Accordingly, the dividing plane 8 is parallel to the Z axis and the optical axis is parallel to the X-axis. The wedge-shaped components 5 and 6 are wedge-shaped in the XY plane.

In the embodiment of the device 10-3 shown in FIGS. 14 and 15, the filters 4a and 4b are not necessarily optical elements from the optics of the collection optics 7, but rather a coating on a first surface 5a of the first wedge-shaped component 5 and a first surface 6a of the second wedge-shaped component 6, respectively. The first surface 5a is the surface of the first wedge-shaped component 5 which is closest to the objective lens 2. Likewise, the first surface 6a is the surface of the second wedge-shaped components 6 which is closest to the objective lens 2.

Additionally, a second surface 5b of the first wedge-shaped component 5 and a second surface 6b of the second wedge-shaped component 6 may be coated with an antireflection coating. The second surfaces 5b and 6b are the respective surfaces of the wedge-shaped components 5 and 6 which are closest to the scene 80. The antireflection coating provides increased sensitivity of the device to the radiation from the scene 80.

Refer now to FIGS. 18A-18B and 19A, an alternative positioning of the filters 4a and 4b. Similar to the embodiment of FIGS. 14 and 15, the filters 4a and 4b are implemented as a coating, but in FIG. 18A the coating is on the second surface 5b of the first wedge-shaped component 5. Similarly, in FIG. 18B, the coating is on the second surface 6b of the second wedge-shaped component 6. In FIG. 19A the coating is on or near the first and second detector regions 1a and 1b. Specifically, the first filter 4a is implemented as a coating on or near the first detector region 1a, and the second filter 4b is implemented as a coating on or near the second detector region 1b.

Refer now to FIG. 19B, an alternative implementation of the filters 4a and 4b. In FIG. 19B, the filters 4a and 4b are implemented as stationary plates positioned in front of, or in direct abutment with, the respective detector regions 1a and 1b.

In the filter alternatives illustrated in FIGS. 18A and 18B, the first surfaces 5a and 6a may be coated with an antireflection coating. In the filter alternatives illustrated in FIGS. 19A and 19B, the first and second surfaces of both wedge-shaped components 5 and 6 are preferably coated with an antireflection coating. It is also noted that for clarity of illustration, the thickness of the coating and plates for implementing the filters 4a and 4b is greatly exaggerated in FIGS. 14, 15, 18A-1B and 19A-19B.

Similar to the devices 10-1, 10-2 and 10-2', the components of the device 10-3 are positioned within a casing defined by internal walls 30 of the device 10-3. Also similar to the devices 10-1, 10-2 and 10-2', the detector array 1 is preferably maintained within a detector case 12.

Figure 17:
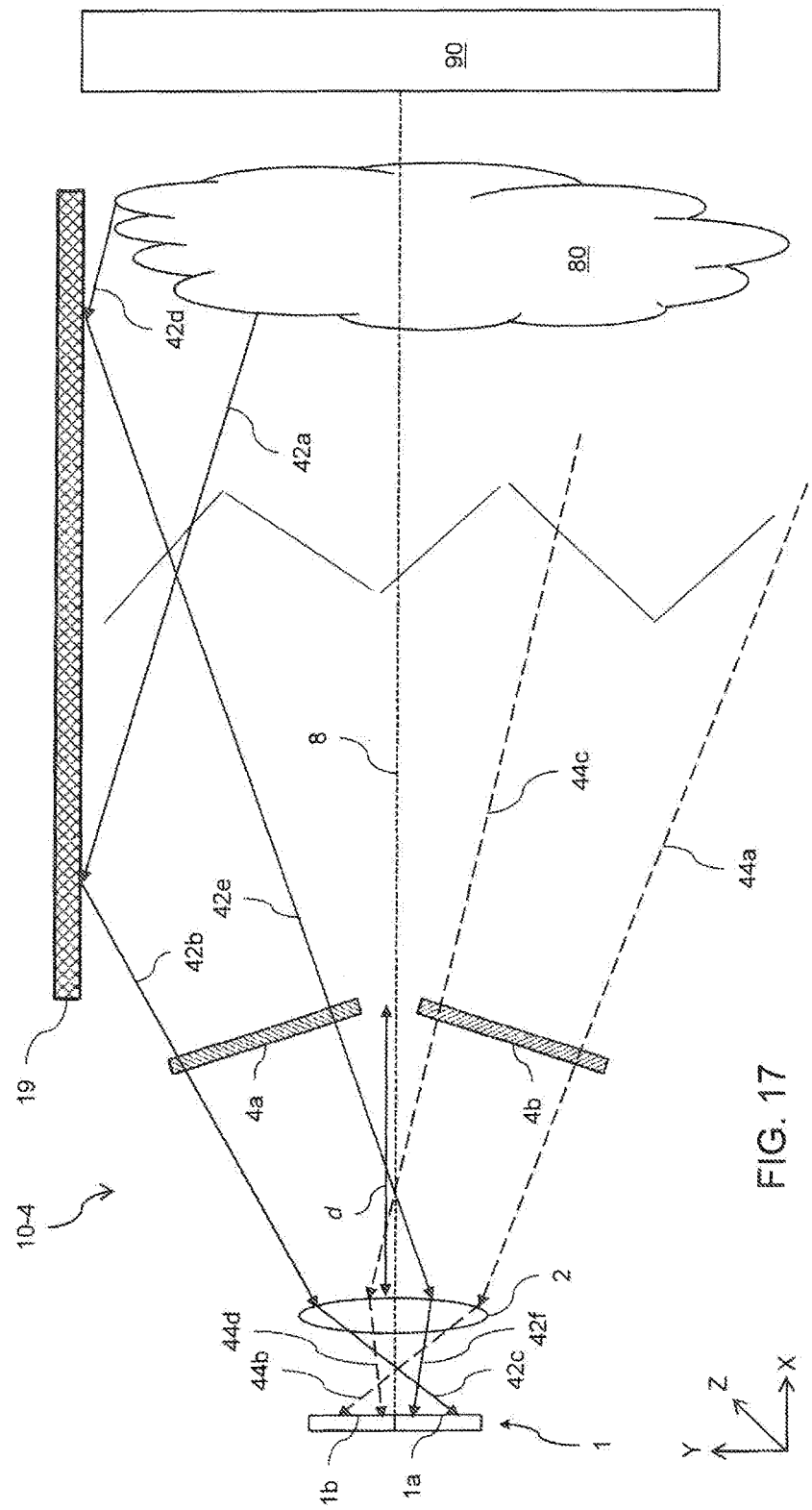
FIG. 17 is a schematic side view illustrating a device with a mirror for detecting and imaging radiation from a scene in two separate wavelength regions without moving parts, according to an embodiment of the invention

3d. Exposure to in-Band and Out-of-Band Filtering by Split Image Mirror Configuration:

A similar result of the device 10-3 may be obtained by using a minor 19 instead of the two wedge-shaped components 5 and 6 described in the previous section 5 (Section 3c). Such a device 10-4 is shown schematically in FIG. 17. In FIG. 17, the minor 19 is positioned with respect to the camera system (i.e., detector array 1) such that the reflective surface of the mirror 19 is perpendicular to the plane of the paper (XY plane) and parallel to the optical axis (X axis). Note that the same Cartesian coordinate system XYZ used in FIG. 14 is also used in FIG. 17.

Although not shown in the drawings, the device 10-4 also includes image acquisition electronics 50 similar to the embodiments of the devices 10-1, 10-2 and 10-2', and 10-3 for generating digital signals and for performing computations and algorithms for determining and/or indicating the presence or absence of the gas cloud path concentration distribution and/or flame, as well as imaging and measuring the gas cloud path concentration distribution and/or flame. Furthermore, although not show in the drawings, the components of the device 10-4 are also positioned within a casing defined by internal walls of the device 10-4 and the detector array 1 is preferably maintained within a detector case, similar to the devices 10-1, 10-2 and 10-2', and 10-3.

FIG. 17 additionally depicts the traversal of incident rays 42a-42f and 44a-44d from the scene 80 to the detector array 1, similar to the depiction of the traversal of rays shown in FIG. 15. The properties of the traversal of the rays depicted in FIG. 17 is generally similar to the properties of the traversal of the rays depicted in FIG. 15 unless expressly stated otherwise and will be understood by analogy thereto. Furthermore, the definitions of the field of view of the device 10-4 and the objective lens 2 of the device 10-4 are generally similar to the definitions provided with respect to the device 10-3 and will also be understood by analogy thereto.

The two filters 4a and 4b are placed either on planes where the two beam bundles are separated (i.e., at the minimum distance d as a function of the aperture diameter of the objective lens and the vertical field of view of the objective lens disclosed in Section 3c and as shown in FIGS. 15 and 17), or directly covering each corresponding region of the detector, similar to the configuration depicted in FIGS. 19A and 19B.

By accordingly positioning the filters 4a and 4b as mentioned above, the device 10-4 maintains a low f-number (fl 1.5 or less) at the detector array 1, similar to that of the device 10-3.

Note that a specific property of the traversal of the rays depicted in FIG. 17 that is different from the traversal of the rays depicted in FIG. 15 is lack of the additional reflected rays which pass through the second filter 4b. Specifically, only 15 the first bundle of rays (42a and 42d) is reflected by the minor 19 before passing through the first filter 4a and the objective lens 2, whereas the second bundle of rays (44a and 44c) is not reflected at all and passes directly through the second filter 4b and the objective lens 2. In other words, the mirror 19 inverts the rays traversing the filter 4a in a vertical upside down direction with respect to the ones of 4b and as a 20 result the two images of the scene 80 formed on the detector array 1 are upside down with respect to each other.

It will be appreciated that the above descriptions are intended only to serve as examples, and that many other embodiments are possible within the scope of the present invention as defined in the appended claims.

What is claimed is:

1. A device for imaging radiation from a scene the radiation including at least a separate first and second wavelength region, the scene including at least one of a first and second material, the first material having spectral characteristics in the first wavelength region and the second material having spectral characteristics in the second wavelength region, the device comprising:
(a) a detector of the radiation from the scene;
(b) a static filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter;
(c) an image forming optical component for forming an image of the scene on the detector, the radiation being imaged simultaneously onto a first and second subset of pixels of the detector, the imaged radiation on the first subset of detector pixels including radiation in the first wavelength region and the imaged radiation on the second subset of detector pixels including radiation in the second wavelength region; and
(d) electronic circuitry electronically coupled to the detector, the electronic circuitry configured to:
(i) produce a pixel signal from each respective detector pixel, each of the pixel signals including information associated with the absorption or emission of radiation in one of the respective wavelength regions by each of the first and second materials, and
(ii) determine the presence or absence of the first and second materials based on the produced pixel signals, wherein indication of the presence or absence of the first and second materials is based on the difference between the pixel signals produced from the first and second subsets of pixels of the detector.

2. The device of claim 1, wherein the first wavelength region includes radiation wavelengths between 3.15 and 3.5 microns, and the second wavelength region includes radiation wavelengths between 4.3 and 4.6 microns.

3. The device of claim 1, wherein the detector includes a separate first and second detector region, the first detector region including the first subset of detector pixels, and the second detector region including the second subset of detector pixels, and the device further comprises:
(e) a radiation directing arrangement for directing radiation from a field of view of the scene through the image forming optical component onto the detector, such that the radiation is separately imaged onto the first and second detector regions.

4. The device of claim 3, wherein the radiation directing arrangement includes a reflective surface positioned substantially parallel to the optical axis of the device.

5. The device of claim 3, wherein the first filter is disposed proximate to the first detector region and the second filter is disposed proximate to the second detector region.

6. The device of claim 3, wherein the first filter is a first plate interposed between the first detector region and the image forming optical component, and the second filter is a second plate interposed between the second detector region and the image forming optical component.

7. The device of claim 3, wherein the first and second wavelength regions are in the mid wave infrared region of the electromagnetic spectrum, and the detector is sensitive to radiation in the first and second wavelength regions.

8. The device of claim 7, wherein the radiation directing arrangement includes first and second substantially wedge-shaped components.

9. The device of claim 8, wherein the first filter is disposed on one of a first surface or a second surface of the first wedge-shaped component, and the second filter is disposed on one of a first surface or a second surface of the second wedge-shaped component.

10. The device of claim 9, wherein the first surface of the first wedge-shaped component is a closest surface of the first wedge-shaped component to the image forming optical component, and the first surface of the second wedge-shaped component is a closest surface of the second wedge-shaped component to the image forming optical component, and the second surface of the first wedge-shaped component is a closest surface of the first wedge-shaped component to the scene, and the second surface of the second wedge-shaped component is a closest surface of the second wedge-shaped component to the scene.

11. The device of claim 1, wherein each of the first and second filters includes a plurality of filter elements, the plurality of filter elements being arranged such that each filter element of the plurality of filter elements of the first filter is adjacent to at least one respective filter element of the plurality of filter elements of the second filter.

12. The device of claim 1, wherein the first material is a hydrocarbon gas cloud and the second material is a flame.

13. The device of claim 12, wherein the electronic circuitry is further configured to:
(iii) if the hydrocarbon gas cloud is present, provide a measurement of the path concentration distribution of the hydrocarbon gas cloud based on at least a portion of the pixel signals.

14. A for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising:
(a) a detector of the radiation from the scene;
(b) a filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter;
(c) an image forming optical component for forming an image of the scene on the detector;
(d) a mechanism for positioning the filtering arrangement relative to the image forming optical component, such that, the radiation is alternately imaged through each of the first and second filters onto the same respective pixels of the detector; and
(e) electronic circuitry electronically coupled to the detector, the electronic circuitry configured to:
(i) produce, from each detector pixel, a respective pixel signal for each alternation of the radiation imaged through the first and second filters, the pixel signals including information associated with the absorption or emission of radiation in one of the respective wavelength regions by each of the first and second materials, and
(ii) determine the presence or absence of the first and second materials based on the produced pixel signals, wherein the indication of the presence or absence of the first and second materials is based on, for each respective pixel of the scene, the averaging of a minority subset of pixel signals produced from the radiation imaged through the first filter, and the averaging of a minority subset of pixel signals produced from the radiation imaged through the second filter.

15. The device of claim 14, wherein the first wavelength region includes radiation wavelengths between 3.15 and 3.5 microns, and the second wavelength region includes radiation wavelengths between 4.3 and 4.6 microns.

16. The device of claim 14, wherein each of the first and second filters includes a plurality of filter elements, the plurality of filter elements being arranged such that each filter element of the plurality of filter elements of the first filter is adjacent to at least one respective filter element of the plurality of filter elements of the second filter.

17. The device of claim 14, wherein the first material is a hydrocarbon gas cloud and the second material is a flame, and wherein the electronic circuitry is further configured to:
  (iii) if the hydrocarbon gas cloud is present, provide a measurement of the path concentration distribution of the hydrocarbon gas cloud based on at least a portion of the pixel signals.

18. The device of claim 14, wherein the first and second wavelength regions are in the mid wave infrared region of the electromagnetic spectrum, and the detector is sensitive to radiation in the first and second wavelength regions.

19. A device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising:
  (a) a detector of the radiation from the scene;
  (b) a static filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter, wherein each of the first and second filters includes a plurality of filter elements, the plurality of filter elements being arranged such that each filter element of the plurality of filter elements of the first filter is adjacent to at least one respective filter element of the plurality of filter elements of the second filter;
  (c) an image forming optical component for forming an image of the scene on the detector, the radiation being imaged simultaneously onto a first and second subset of pixels of the detector, the imaged radiation on the first subset of detector pixels including radiation in the first wavelength region and the imaged radiation on the second subset of detector pixels including radiation in the second wavelength region; and
  (d) electronic circuitry electronically coupled to the detector, the electronic circuitry configured to:
    (i) produce a pixel signal from each respective detector pixel, each of the pixel signals including information associated with the absorption or emission of radiation in one of the respective wavelength regions by each of the first and second materials, and
    (ii) determine the presence or absence of the first and second materials based on the produced pixel signals.

20. A device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising:
  (a) a detector of the radiation from the scene;
  (b) a filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter, wherein each of the first and second filters includes a plurality of filter elements, the plurality of filter elements being arranged such that each filter element of the plurality of filter elements of the first filter is adjacent to at least one respective filter element of the plurality of filter elements of the second filter;
  (c) an image forming optical component for forming an image of the scene on the detector;
  (d) a mechanism for positioning the filtering arrangement relative to the image forming optical component, such that, the radiation is alternately imaged through each of the first and second filters onto the same respective pixels of the detector; and
  (e) electronic circuitry electronically coupled to the detector, the electronic circuitry configured to:
    (i) produce, from each detector pixel, a respective pixel signal for each alternation of the radiation imaged through the first and second filters, the pixel signals including information associated with the absorption or emission of radiation in one of the respective wavelength regions by each of the first and second materials, and
    (ii) determine the presence or absence of the first and second materials based on the produced pixel signals.

\* \* \* \* \*